United States Patent [19]

Harris, Jr.

[11] 4,000,654
[45] Jan. 4, 1977

[54] AUTOMATIC FLUID INJECTOR

[76] Inventor: Rano J. Harris, Jr., 4423 S. Park Drive, Baton Rouge, La. 70816

[22] Filed: Oct. 1, 1975

[21] Appl. No.: 618,374

[52] U.S. Cl. .......................... 73/422 GC; 73/423 R
[51] Int. Cl.[2] ........................................ G01N 1/02
[58] Field of Search .......... 73/421, 422 R, 422 GC, 73/423 A

[56] References Cited

UNITED STATES PATENTS

| | | | |
|---|---|---|---|
| 3,401,565 | 9/1968 | Stoll et al. | 73/422 |
| 3,841,160 | 10/1974 | Iwao | 73/422 |
| 3,885,438 | 5/1975 | Harris et al. | 73/422 |

*Primary Examiner*—S. Clement Swisher
*Attorney, Agent, or Firm*—Llewellyn A. Proctor

[57] ABSTRACT

An improved automatic fluid injector, or syringe, for accurately measuring and injecting quantities of fluid specimens, or samples, into various media, e.g., a receptacle or inlet of a modern analytical instrument. The apparatus includes the general combination of (a) an injector, or syringe sub-assembly, inclusive of a needle syringe provided with a forward mounted needle and rearwardly mounted reciprocable plunger, (b) an injector feed sub-assembly provided with a reciprocable hollow probe, or probes, for pick-up of a fluid specimen for use in purging, cleaning and filling said syringe, and (c) a magazine, or feed tray, for transporting fluid specimen containing vials and positioning same relative to the injector feed assembly for pick-up of the fluid specimen, and delivery to the syringe. Sub-assembly (a), inclusive of a plunger actuation means, is mounted upon a plate slidable upon a base plate, and means are also mounted upon said base plate for actuation and reciprocation of said slide plate for thrust of the dispensing end of the needle of the syringe into a tubular member, provided with a sealed entry feature, adjacent the inlet to the analytical instrument. Sub-assemblies (b) and (c) are also mounted upon the base plate, sub-assembly (b) picking up a fluid specimen from (c) for delivery to said tubular member at which location fluid specimen is transferred to the syringe of sub-assembly (a).

10 Claims, 16 Drawing Figures

AUTOMATIC FLUID INJECTOR

RELATED APPLICATIONS

This application is related to the subject matter covered in U.S. Pat. No. 3,754,443 granted on Application Ser. No. 233,663 filed Feb. 4, 1972; U.S. Pat. No. 3,885,438 granted on Application Ser. No. 365,552 filed May 31, 1973; U.S. Pat. No. 3,824,859 granted on Application Ser. No. 333,120 filed Feb. 16, 1973; and Application Ser. No. 584,134 filed Sept. 9, 1974, the disclosures of which are herewith referred to and fully incorporated by reference.

The present invention relates generally to automatic fluid injectors, or apparatus, for automatically measuring and injecting accurately measured quantities of fluids. More particularly, it relates to apparatus, especially fluid injection devices or syringes, for continuous automatic measurement and injection of very small, accurately measured quantities of gas and liquid specimens into various media, e.g., modern analytical instruments.

Fluid injection devices, particularly needle syringes, have gained wide acceptance by the industry, and by the scientific community, generally, for use in dispensing infinitesimally small, accurately measured fluid specimens, e.g., to modern analytical instruments such as mass spectrometers and gas chromatographs. Such syringes embody apparatus comprising a tubular body or barrel, on the forward end of which is fitted a hollow or tubular needle and, at the opposite end, a slidable plunger which travels within the bore of the barrel. Syringes of such character, and related devices, are capable of dispensing very small fluid specimens, accurately measured, on the order of a few microliters, or very small fractions of a microliter, e.g., from about 0.01 to about 5 microliters, or fractional parts thereof.

In recent years, due to the obvious advantages offered by the combination of automatic fluid injection instruments, and modern data gathering techniques, which greatly reduce operating manpower without decrease in accuracy, there is considerable demand for improved automatic devices of these types.

It is, accordingly, a primary object of the present invention to provide new and novel fluid injectors readily adaptable to automatically perform the basic cyclic functions of purging and cleaning, filling, and injecting.

A particular object is to provide apparatus capable of continuously cyclically serially withdrawing precisely measured, infinitesimally small quantities of gas or liquid specimens from prefilled vials or containers, injecting the specimens in seriatim in reproducible quantities, and cleaning prior to subsequent withdrawal and injection of a subsequent specimen.

A further object is to provide apparatus of simple and relatively inexpensive construction, particularly apparatus which can be readily serviced and operated, which apparatus readily lends itself to rapid mass production techniques.

Yet another object is to provide apparatus which embodies further improvements over those devices specifically disclosed and claimed in U.S. Pat. Nos. 3,885,438; 3,824,859; 3,754,443 and Application Ser. No. 584,134, supra.

These and other objects are achieved in accordance with the present invention which embodies improvements in automatic fluid injector systems. A preferred type of automatic fluid injector is comprised generally of (a) an injector, or syringe sub-assembly, inclusive of a needle syringe, (b) an injector feed sub-assembly, provided with a reciprocatable hollow probe, or probes, for pick-up of a fluid specimen for use in purging, cleaning and filling said syringe, and (c) a magazine, or feed tray, for transporting fluid specimen containing vials and positioning same in relation to the injector feed assembly for pick-up of the fluid specimen by said probe, or probes for delivery to the syringe. The automatic fluid injector also includes automation or control means for repetitively and automatically carrying out the functions of cleaning, purging and filling the syringe with predetermined quantities of fluid specimens and for subsequent injection, all in timed sequence. The several sub-assemblies of the automatic fluid injector are generally contained within a housing.

(a) The injector, or syringe sub-assembly, per se includes generally a needle syringe, inclusive of means for actuation and reciprocation of the plunger of said syringe, both the syringe and plunger actuation and reciprocation means being mounted upon a plate which is slidably maintained atop a base plate constituting a portion of the housing. The slide plate per se, inclusive of the needle syringe and plunger actuation and reciprocation means, is movable by virtue of actuating means mounted on said base plate for reciprocal movement thereof on a straight line path along the surface of the base plate.

The injector, or syringe sub-assembly per se, also includes a tubular member mounted on said base plate. This member is provided with an opening which contains a tubular seal, the axial opening of which is aligned upon an inlet which leads into a media within which a fluid specimen is to be injected, e.g., an analytical instrument. The axial opening of the seal is also communicated with a lateral opening within the seal, and tubular member, such that the dispensing end of the needle of the syringe can be inserted into the axial opening of the seal, and a fluid specimen can be transferred from the magazine or feed tray via the injector feed sub-assembly through the lateral opening to the needle for filling the syringe.

(b) The injector feed sub-assembly, the function of which is to obtain a fluid specimen from a vial carried by the magazine or feed tray, is mounted upon the base plate in generally vertical orientation therewith. It is comprised generally of a reciprocable hollow probe, or probes, associated with means which enable said probe to be projected into the source of fluid specimen to act as a conduit for receipt and transfer of the fluid which is supplied thereto under a slight pressure, which acts as a driving force to transfer the fluid, and fill the syringe, It is quite feasible to employ a single hollow probe to carry out the function of transferring the fluid specimen from a vial, or a pair of probes can be employed; and where a pair of probes are employed, one probe is used as a conduit for carrying a pressurized fluid to pressurize a vial, while the other is employed to physically transfer the fluid specimen. Where two probes are employed, the probes can be concentrically mounted or mounted in parallel relationship.

(c) The magazine, or feed tray, can carry or transport one or a plurality of vials for pick-up by the probe for delivery to the syringe. One type of feed tray is described by reference to U.S. Pat. No. 3,754,443, herewith incorporated by reference. A more preferred type, however, is subsequently described in detail.

The characteristics of a preferred automatic fluid injector, or syringe, and the principle of its operation, will be more fully understood by reference to the following detailed description of preferred embodiments, and to the attached drawings to which reference is made as the description unfolds. Similar numbers are used to represent similar parts or components in the several figures. Subscripts are used where there is a plurality of similar parts, or components.

Referring to the figures, particularly to FIGS. 1 through 5, there is described a preferred type of automatic fluid injector, or syringe 100. In general, referring initially to FIG. 1, the principal components of the automatic fluid injector 100 includes (a) an injector, or syringe sub-assembly 10, inclusive of plunger adjustment means 20 and plunger drive, or actuating mechanism 30, which elements are mounted atop a slide plate 40 located upon a larger base plate 50, the base plate 50 constituting a portion of the casing or housing within which the components are normally contained. An injector, or syringe drive mechanism 60, is also directly mounted on the upper side of base plate 50, a reciprocable piston 51 of which is operatively connected via a mounting bracket 52 to the slide plate 40 for effecting reciprocable movement of the slide plate 40. The automatic fluid injector 100 also includes, referring particularly to FIG. 2, (b) an injector feed sub-assembly 70 for use in purging, cleaning and filling the injector, or syringe 11, and (c) a magazine sub-assembly 90, best shown by reference to FIG. 3 for receipt, transport, and positioning of vials which contain fluid specimens, for pick-up of fluid specimen therefrom for delivery to the injector, or syringe 11 via the action of the injector feed sub-assembly 70. Both the injector feed sub-assembly 70 and magazine sub-assembly 90 are generally vertically mounted upon the base plate 50. These several sub-assemblies (a), (b) and (c) are responsive to automatic control means such as described, e.g., by reference to U.S. Pat. No. 3,754,443 herewith incorporated by reference.

The principle features, and function, of these several sub-assemblies are generally as follows:

a. The injector, or syringe sub-assembly 10, whose principle purpose is to measure out and deliver a fluid specimen, includes generally a needle syringe 11 comprised of a hollow or tubular barrel 12, provided with a side opening $12_1$, a cannula or needle 13 mounted within the front end thereof, and a slidable plunger 14 mounted within the opposite, or rearward end of the barrel 12. The syringe 11 is itself mounted within a segmented block 15, upwardly notched at both ends, within which the tubular barrel portion 12 of the syringe 11 is fitted. The forward face of the flanged rearward portion $12_2$ of the barrel 12 is fitted against the rearward side of the block (a segmented portion which is bolted to the forward portion of the block) to aid in preventing or restricting any possible forward movement of syringe 11. The forward end of block 15 is provided with a hollow passage leading from the upward face of said block 15 to an exit location on a side of the block 15. The forward portion of barrel 12 is provided with a short tubular segment 16 which is fitted within the opening $12_1$ and is extended downwardly through a tubular seal 17 for communication with the side exit 18 located within the right front face of the block 15. The block 15 is secured in fixed position on the upper side of the slide plate 40.

The injector, or syringe sub-assembly 10, also includes means for actuating and driving the plunger, which plunger drive, or actuating mechanism, is also mounted upon the slide plate 40. The plunger drive, or actuating mechanism, suitably a fluid actuatable double acting cylinder piston unit 30 inclusive of a piston 31 which is connected via a bracket 32 to the plunger 14 of syringe 11. Reciprocation of the piston 31 produces reciprocal movement of the plunger 14, without corresponding movement of the syringe 11, or slide plate 40. Thus, the knurled knob or handle $14_1$ of plunger 14 is fitted within a notched portion of the bracket 32, and adjustably but rigidly held therein by means of a clamping screw 19, and the other end of the Z-shaped bracket is rigidly secured upon an end of piston 31. Both the double acting cylinder piston unit 30 and the bracket 32, like syringe 11, are also mounted upon the slide plate 40, as suggested. Reciprocal movement of the piston 31, as occurs when a pressurized fluid such as air is alternately injected into lines 33, 34 of the cylinder piston unit 30, produces a corresponding reciprocation of the plunger 14.

Means for adjusting the distance of movement of the plunger 14 are also provided, and located upon the slide plate 40. Suitable mechanisms for adjusting the length of the plunger stroke are described by reference to any of Applications Ser. No. 333,120 (now U. S. Pat. No. 3,824,859); Ser. No. 365,552 (now U. S. Pat. No. 3,885,436) and Ser. No. 584,134, now allowed. A further device particularly suitable for this purpose is plunger adjustment means 20, perhaps best shown by reference to FIGS. 1, 2, 4 and 5, but particularly by reference to FIG. 13. The plunger adjustment means 20 is comprised essentially of a hollow member, or block 24, which is adjustably, but which can be secured or locked in fixed position within the path of movement of the plunger 14 such that its movement is physically restricted to traverse a predetermined, or pre-set, distance. A preferred plunger adjustment means 20 thus includes a hollow member, or block 24, which is adjustably movable within the slot 41 of plate 40, on which it is mounted, and which can be fixed in any desired position along the slot 41 of slide plate 40 via a bolt 21, one end of which is provided with a knurled knob 22 and the other end of which is externally threaded for receipt of a nut 23. In a preselected fixed position, the block 24 physically blocks, and restricts, backward movement of the plunger 14 by impingement upon bracket 32, but forward movement of the plunger 14 is restricted only by the length of the plunger 14 and the length of the barrel 12.

Figure 1:
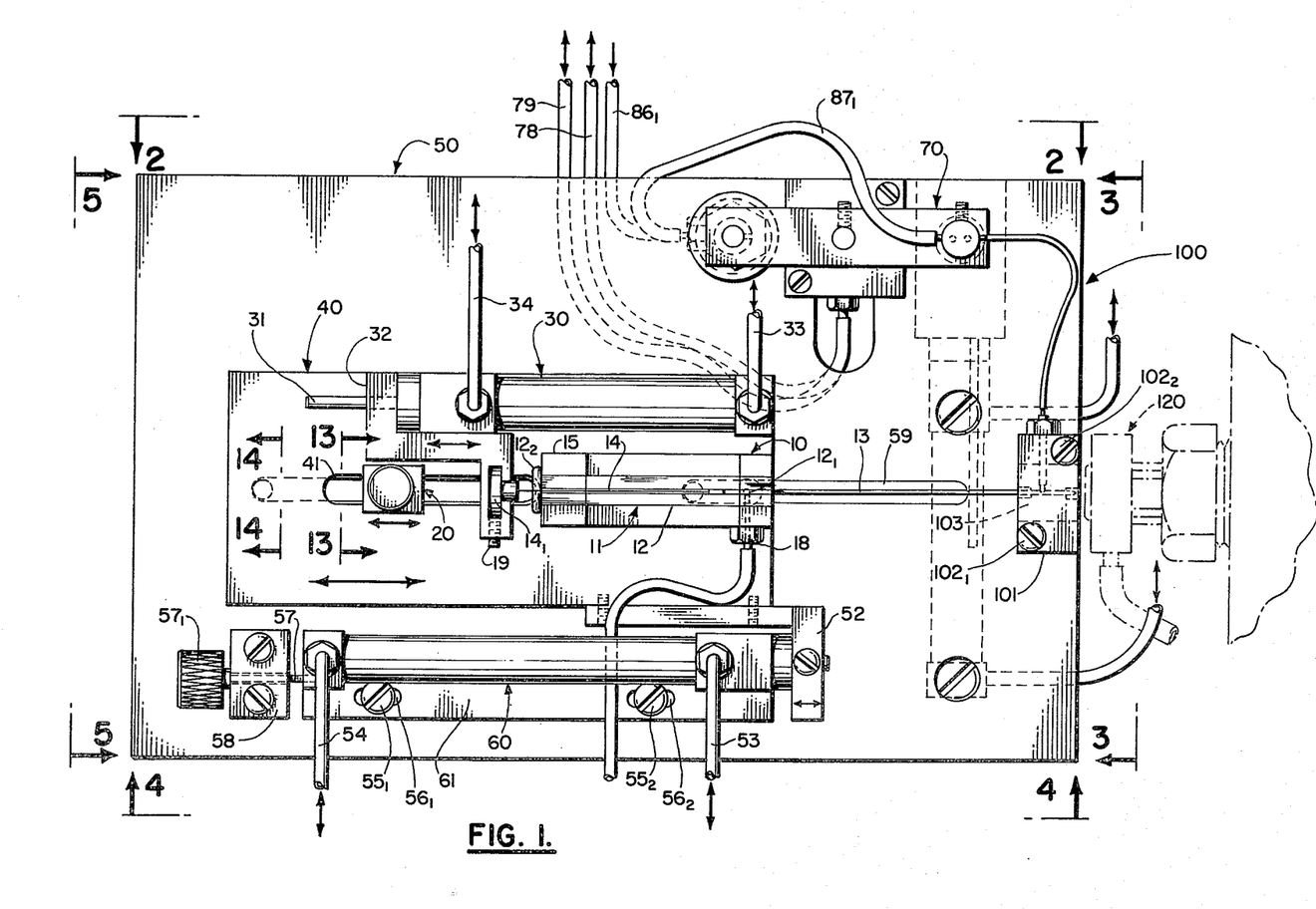
FIG. 1 depicts a top plan view of a preferred automatic fluid injector, or syringe, the essential elements of which are mounted upon a base plate, inclusive of the said syringe, and plunger adjustment and plunger drive mechanism, which are mounted upon a slide plate which rides upon the base plate, and which, in turn, is aligned upon a septum inlet into which the needle portion of the syringe can be inserted for delivery of an accurately measured fluid specimen.
Figures 4, 5:
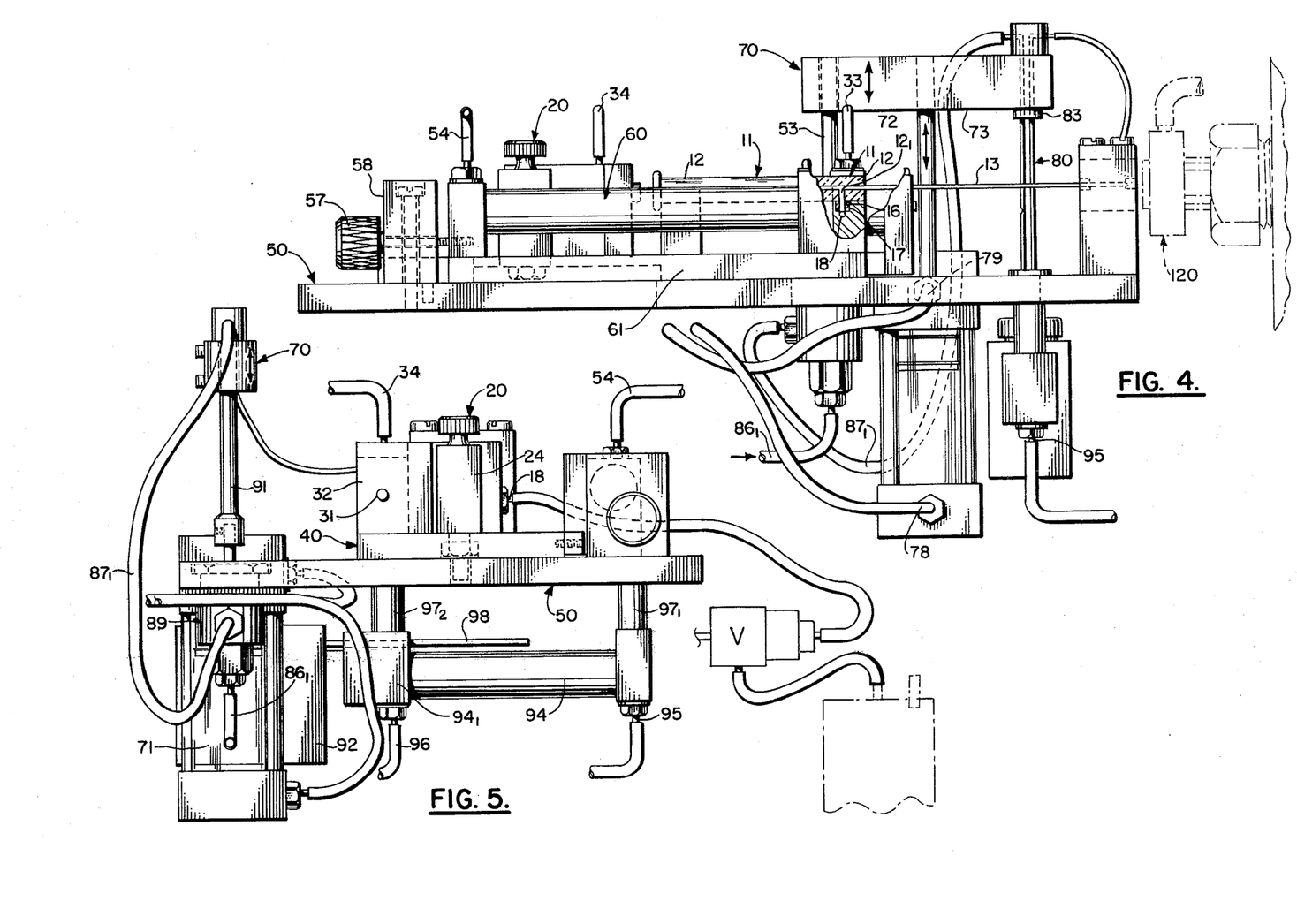
FIG. 4 is an elevation view from the opposite side of that depicted with reference to FIG. 2, the view being that seen from the plane cut by line 4—4 of FIG. 1.
FIG. 5 is a left end and view of said automatic fluid injector, the view being that seen from the plane cut by line 5—5 of FIG. 1.
Figure 14:
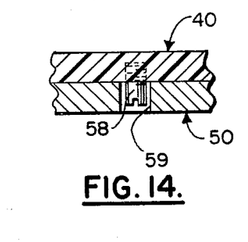
FIG. 14 is a fragmentary view in partial cross-section of guide means which maintain the alignment of the slide plate, which carries the injector, plunger adjustment and plunger drive mechanism, with the base plate on which the slide plate is mounted; the view being a section taken along line 14—14 of FIG. 1.

A syringe drive mechanism, suitably a double acting suitably a double acting cylinder piston unit 60, is also a component of the component injector, or syrine sub-assembly 10. The function of the cylinder piston unit 60 is to reciprocate the entire slide plate 40 along a guided path for insertion of the needle 13 of syringe 11 into a suitable septum inlet 120 into which a preselected accurately measured quantity of a fluid specimen is to be injected. Referring specifically to FIGS. 1 and 4, it will be observed that the cylinder piston unit 60 is rigidly mounted and directly secured upon a mounting plate 61 bolted upon the base plate 50. The base plate 50, upon which the mounting plate 61 is bolted, it will be observed, is provided with a guide slot 59 (or pair of aligned guide slots, not shown) within the slide plate 40 is slidably mounted. A downwardly projecting screw head (or pair of screw heads, one extending into each of the pair of guide slots, not shown) aids in maintaining such alignment as illustrated by reference to FIG. 14. Thus, a downwardly projecting screw 58, secured upon slide plate 40, extends into and is slidably movable along the length of slot 59 of base plate 50. Referring back to FIGS. 1 and 4, it will be observed that the slide plate 40 is maintained in contact with the base plate 50 by means of the mounting bracket 52. The mounting bracket 52 is bolted to the plate 40, and it rigidly secures the slide plate 40 in place. Slide plate 40 is reciprocated along the path of guide slot 59 via alternate injections of a pressurized fluid into lines 56, 54 to reciprocate piston 51 (FIG. 11) to which the slide plate 40 is secured via the mounting bracket 52. The forward (or rearward) extent of movement of slide plate 40 can be set, or adjusted, by loosening of the set screws $55_1, 55_2$ within the elongated slot openings $56_1, 56_2$, and then rotating the knob $57_1$ of set screw 57 which extends (or retracts) the screw relative to the fixed block 58 to slide and reposition the mounting plate 61 (which carries cylinder piston unit 60), after which time the screws $55_1, 55_2$ are retightened in place.

Figures 2, 3:
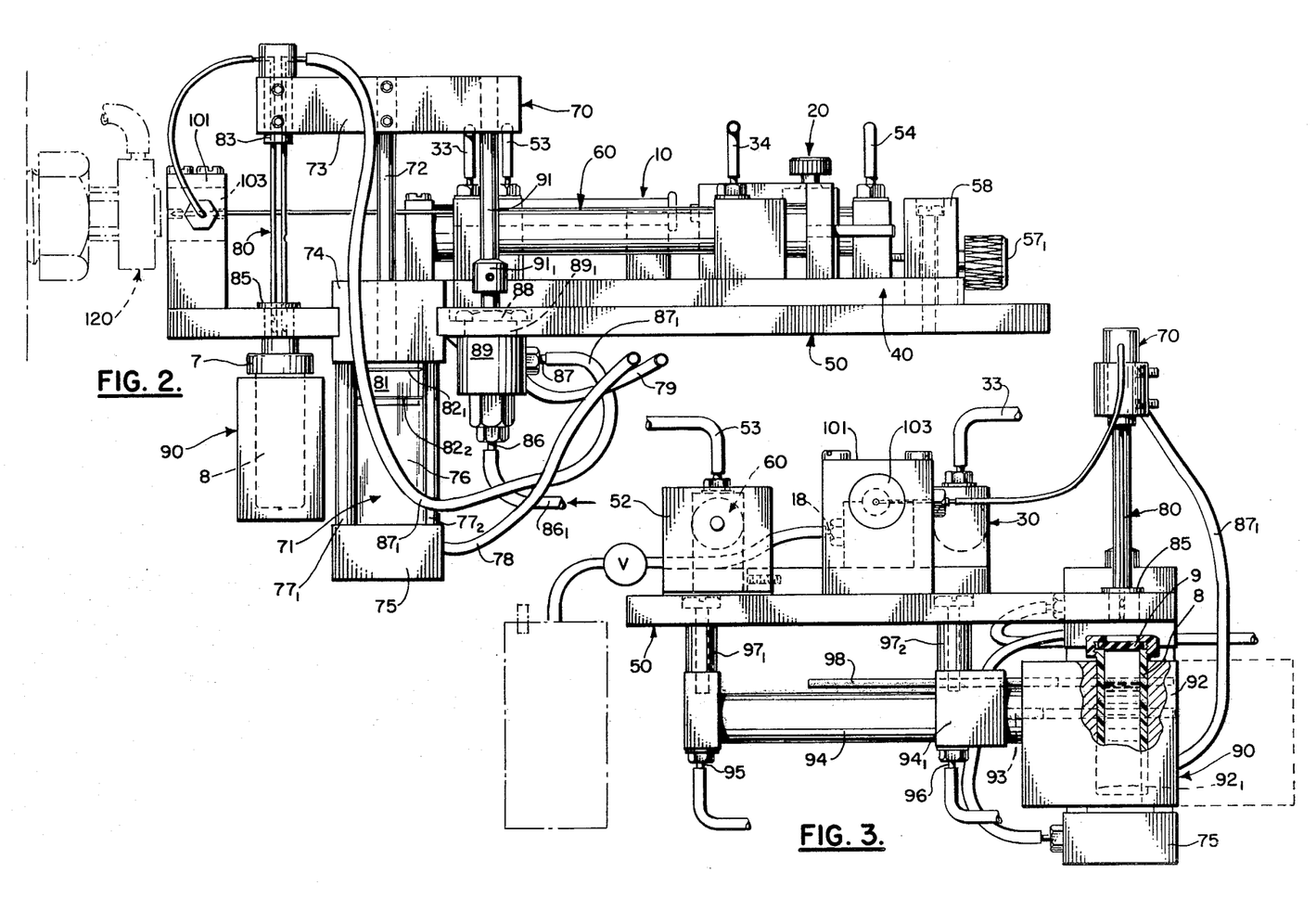
FIG. 2 is a side elevation view of said automatic fluid injector, the view being a view taken along line 2—2 of FIG. 1.
FIG. 3 is a right end view of said automatic fluid injector, the view being taken along line 3—3 of FIG. 1.

(b) The purpose and function of the injector feed sub-assembly 70 is to transfer a fluid specimen from a vial, transported by the magazine and suitably positioned for pick-up and delivery, for use in purging, cleaning and filling the syringe 12. The injector feed sub-assembly 70, generally described by reference to FIG. 2, is directly mounted upon and in a plane substantially vertical to that of the base plate 50. This assembly includes generally a double acting cylinder piston unit 71, upon an end of the upwardly oriented piston 72 of which is mounted a cross beam 73. One side of the cross beam 73 carries a probe, or probe assembly 80, and the other is employed for actuation of a valve 89 which is affixed upon the base plate 50.

The upper end of the cylinder piston unit 71, it will be observed, is constituted of a cube shaped block 74, provided with a central opening, which is integrally mounted within the base plate 50. The lower end of the cylinder piston unit 71 is constituted of a block 75 of substantially the same cross section (on planes parallel or corresponding with that of base plate 50). The lower and upper faces, respectively, of blocks 74, 75 are provided with circular shaped seats within which is seated and contained the terminal ends of tubular member 76 (shown in the figures as constituted of a transparent plastic material), and the blocks 74, 75 are rigidly held by a pair of bars $77_1, 77_2$ in spaced relationship. A pressurized fluid, e.g., air, alternately injected via lines 78, 79 into the cylinder 76 to alternately impinge upon opposite faces of the piston head 81 (sealed within the cylinder 76 via sealing 0-rings $82_1, 82_2$ 3 produces vertical reciprocation of the piston 72.

Figure 15:
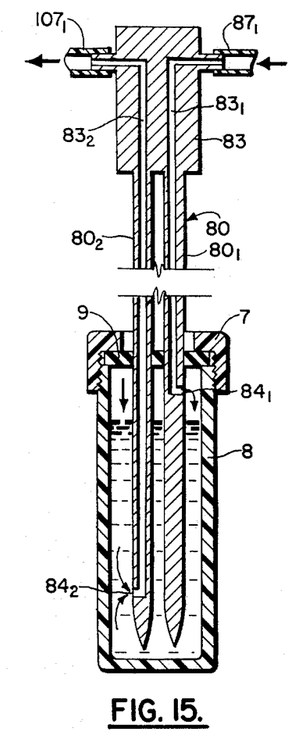
FIG. 15 is a preferred type of probe assembly for use in the pick-up and delivery of a fluid specimen from a vial carried by the feed magazine.

The probe, or probe assembly 80, shown in detail by reference to FIG. 15, is constituted of a pair of hollow needles $80_1, 80_2$ affixed parallel one to the other within the cylindrical section 83 which is mounted upon the cross bar 73. The hollow needles are provided with upper connecting conduits $83_1, 83_2$, respectively, in cylindrical section 83 which terminate in nozzles to which flexible conduits are attached, and lower communicating side openings $84_1, 84_2$, respectively. In downward descent of the probe assembly 80, the pointed or tapered ends of the hollow needles $80_1, 80_2$ pass through parallel aligned openings within a tubular seal 85 contained within an opening through base plate 50. The needles $80_1, 80_2$ penetrate the septum 9, held in place on the top and across the shoulders of a vial 8 by the open cap 7, as shown. A pressurized gas, e.g., air or nitrogen, is passed into the vial 8 through the openings $83_1, 84_1$ of the first needle $80_1$ to pressurize the vial 8, thus causing the fluid specimen contained in the vial to enter needle opening $84_2$ of the second needle $80_2$ for passage through the conduit $83_2$.

Figure 16:
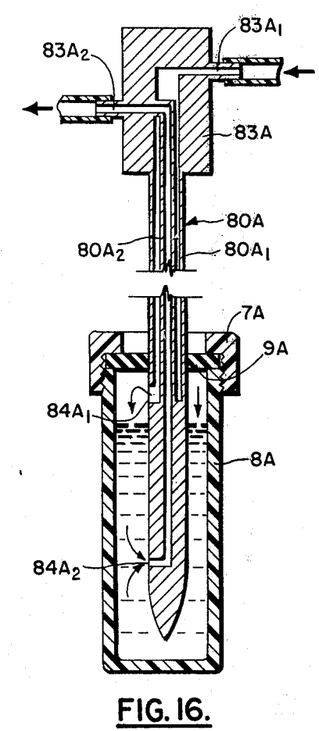
FIG. 16 is another preferred type of probe assembly.

An alternate, and preferred, type of probe or probe assembly 80A is shown by reference to FIG. 16. In this probe assembly, the hollow needles $80A_1, 80A_2$ are concentrically mounted in cylindrical member 83A. The outer needle $80A_1$ opens to the vial 8A, provided with a septum 9A and open centered cap 7A, via the lower side opening $84A_1$ and the inner needle $80A_2$ opens to the vial 8A via the lowermost side opening $84A_2$. The upper opening $83A_2$ is in direct communication through the hollow needle $80A_2$ with lower opening $84A_2$, and the upper opening $83A_1$ is in direct communication through the hollow needle $80A_1$ with lower opening $84A_1$. Pressurizing fluid through $83A_1$ of needle $80A_1$ exits from the lower needle opening $84A_1$, and fluid specimen from the vial 8A is forced into the opening $84A_2$ of needle $80A_2$ to exit therefrom via opening $83A_2$.

The valve 89, of the on-off type, constitutes a regulated source of pressurized gas for transfer of a fluid specimen from vial 8 by the probe, or probe assembly 80 (or 80A). Referring for convenience, e.g., to FIG. 2, it will be observed that the valve 89 is rigidly mounted via passage of a relatively small upper externally threaded end $89_1$ through an opening in plate 50, to which it is secured in vertical orientation via a nut 88. The valve 89 is provided with a gas inlet 86 and a primary gas outlet 87, both of which are provided with flexible hose connections $86_1, 87_1$. The flexible gas inlet hose $86_1$ is from a pressurized source of gas, not shown, and the flexible gas outlet hose $87_1$ is connected to a nozzle connection $83_1$ on cylindrical member 83 (FIG. 15). The stem 91 of valve 89 is biased in raised position, the upper end thereof being slidably mounted through an opening within an end of cross beam 73. In this position the valve 89 is closed so that an inlet gas entering gas inlet 86 is passed via primary gas outlet 87, via hose connection $87_1$ to nozzle connection $83_1$ of cylindrical member 83 (FIG. 15). This condition prevails as the cross beam 73 (and probe assembly 80) descends. On sufficient downward movement, however, the end of cross beam 73 impinges upon the enlarged stem portion $91_1$ such that the stem 91, which acts as a guide, is moved downward to open the valve, and a flow of pressurized gas to the primary gas inlet 86 is initiated, this occurring as the needles $80_1, 80_2$ reach a location adjacent the bottom of vial 8. The valve 89 is again closed on ascent of cross beam 73 sufficient to disengage or break contact with the enlarged stem portion $91_1$.

The injector or syringe sub-assembly 10, as earlier suggested also includes a generally tubular member, or block 101, this constituting the location at which the fluid specimen obtained by the probe 80 from a vial 8 is injected into the syringe 12. The block 101 (FIG. 9) is thus provided with an opening within which a tubular seal 103 is inserted, the block 101 being secured upon the base 50 via bolts $102_1, 102_2$. The block 101 is also provided with a side conduit or channel 104 contiguous and communicated with a side opening or channel 105 within the tubular seal 103, the channel 105 being communicated with central opening 106, provided with slightly enlarged open ends $106_1, 106_2$ to facilitate entry and withdrawal of the needle 13 of syringe 12. It will be observed (particularly by continued reference to FIG. 9) that a fluid specimen which enters nozzle inlet 107, via line $107_1$, can be passed through channels 104, 105 into the side opening $13_1$ of needle 13, and conveyed through the hollow needle to the opening $12_1$ at the front end of the syringe barrel. With the plunger 14 withdrawn, as in a cleaning and purging operation, the fluid will pass via outlets 16, 18 to the exterior.

(c) The magazine, or feed tray 90, whose chief function it is to transport a fluid specimen containing vial, or vials, to a location for pick-up by the probe, or probe assembly 70, can be one of several types, as described, e.g., in related applications or patents, supra. A preferred type of magazine, or feed tray 90, best described by reference to FIG. 3, is mounted on the lower side of the base plate 50 and in a plane perpendicular to that formed by the base plate 50. The magazine, or feed tray 90, comprises a receptacle 92 provided with one or more in-line openings $92_1$ for receipt and containment of fluid specimen containing vials 8, such as described by reference to FIG. 15 (or FIG. 16). The receptacle 92 is mounted on a drive mechanism, suitably on an end of a piston 93 of a double acting cylinder piston unit 94, appended via posts $97_1, 97_2$ from base plate 50 to which it is bolted. The cylinder piston unit 94 and the receptacle 92 are mounted in line, such that on the reciprocation of piston 93 as occurs by alternate injections of a pressurized fluid into lines 95, 96. The septum portion 9 of a fluid specimen containing vial 8 is located, in a first position, directly below the tubular packing 85 through which the needles $80_1, 80_2$ of probe assembly 80 can be projected on descent of said assembly. In a second position (shown by phantom lines), the receptacle 92 is projected outwardly, as by injection of pressurized air into line 95, so that the discharged vial 8 can be replaced by a freshly filled vial. The precise alignment of the receptacle 92 and the double acting cylinder piston unit 94 is maintained by virtue of a guide bar 98 rigidly affixed upon the receptacle 92, and slidably mounted within an opening through the forward wall portion $94_1$ of the double acting cylinder piston unit 94.

Figure 6:
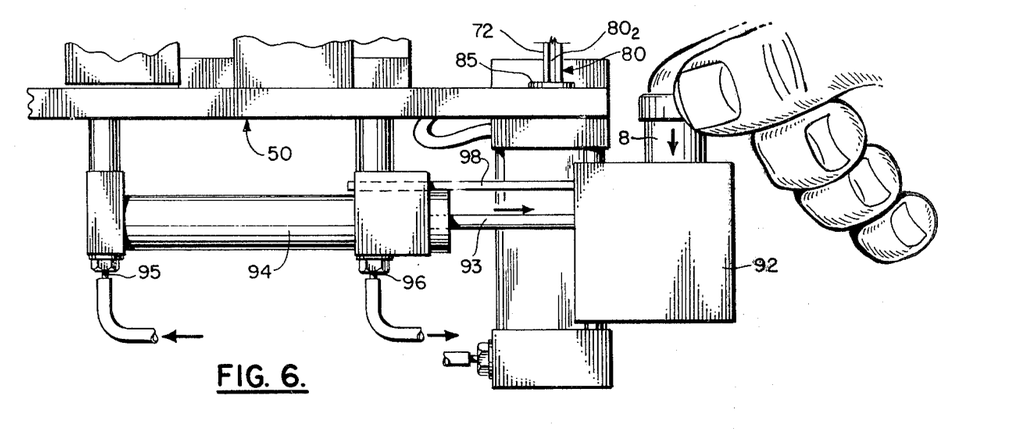
FIG. 6, which corresponds in part with that view illustrated by reference to FIG. 3, depicts in some further detail the loading, and the operation and function of the sample delivery and feed mechanism.

An operating cycle is best described by reference to FIGS. 6 through 16. These figures, taken in connection with preceding FIGS. 1 through 5 to which reference is also made, illustrate the operations involved in loading the magazine, in cleaning, purging and filling the syringe, and in delivering an accurately measured fluid specimen to the septum inlet of, e.g., an automatic instrument. The starting position of the several sub-assemblies constituting the automatic fluid sampler is described by reference to FIGS. 1 through 5. The time sequence of operation of these various sub-assemblies, which can be repeated ad infinitum, is as follows:

a. Referring to FIG. 6, actuation of cylinder piston unit 94 via injection of pressurized air into line 95 thrusts magazine 92 outwardly from under base plate 50, making the opening within the magazine 92 accessible so that a vial 8 can be loaded therein. On the outward thrust of magazine 92, air is ejected from line 96 of cylinder piston unit 94. After the vial 8 is loaded therein, the magazine 92 is repositioned by injection of pressurized air into line 96, the vial 8 at this time being positioned so that its septum 9A (FIG. 15) is directly below the pair of probes $80_1, 80_2$ for subsequent penetration and entry into said vial 8. On withdrawal of magazine 92, air is exhausted from line 95 of the cylinder piston unit 94.

Figures 7, 8:
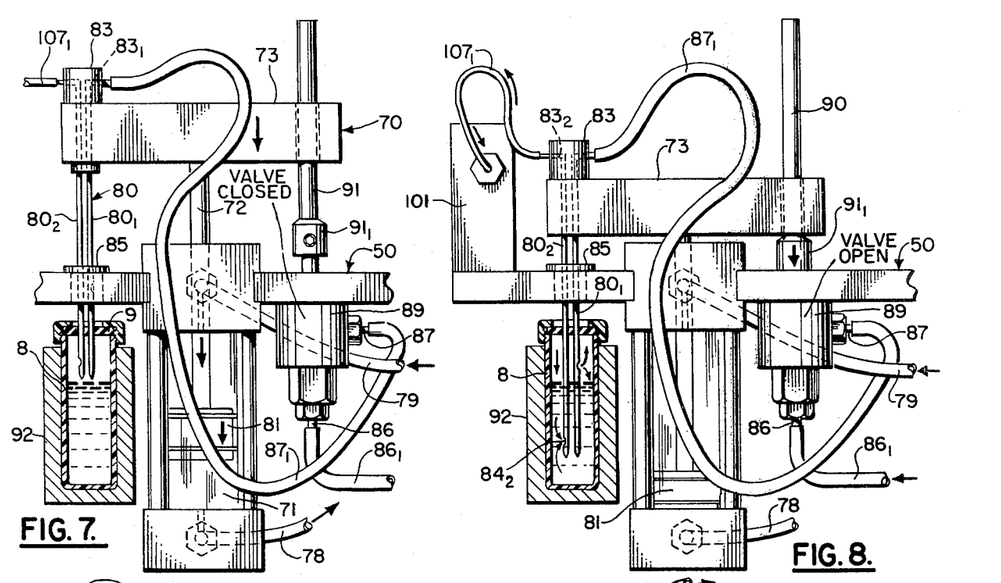
FIGS. 7 and 8, taken in connection with FIG. 6, depict in partial section the mechanism by virtue of which a fluid specimen, or sample, is taken from a vial delivered by said feed mechanism and delivered to the injector or syringe.

(b) Referring to FIG. 7, pressurized air is injected into the double acting cylinder piston unit 71 via entry therein through line 79, the air impinging upon the upper face of piston head 81 to drive the piston 72 downward. As this occurs, air is exhausted from the opposite side of cylinder piston 71 via line 78. On downward movement of piston 72, the probes $80_1, 80_2$ pass through the parallel openings in seal 85, enter into and pierce the septum 9 of vial 8, contained within magazine 92.

(c) Referring to FIG. 8, as probe 80 approaches the maximum extent of its downward movement, the side of cross bar 73 slidably mounted upon stem 91 contacts the enlarged stem portion 91. As this occurs, pressurized gas, e.g., air or nitrogen, is injected via primary inlet 86 of valve 89, and passes via gas outlet 87, tubing $87_1$, to the nozzle inlet $83_1$ and enters via probe $80_1$ into vial 8. The contents of vial 8 are pressurized as the probe 80 continues its descent. Valved line 18 (FIG. 9), previously closed, is now opened and the pressurized gas within vial 8 forces the fluid specimen into the lower inlet $84_2$, the liquid passing therethrough, via passage $83_2$ of the cylindrical member 83 and tubing $107_1$ to enter into passageway 104 of block 101.

Figure 9:
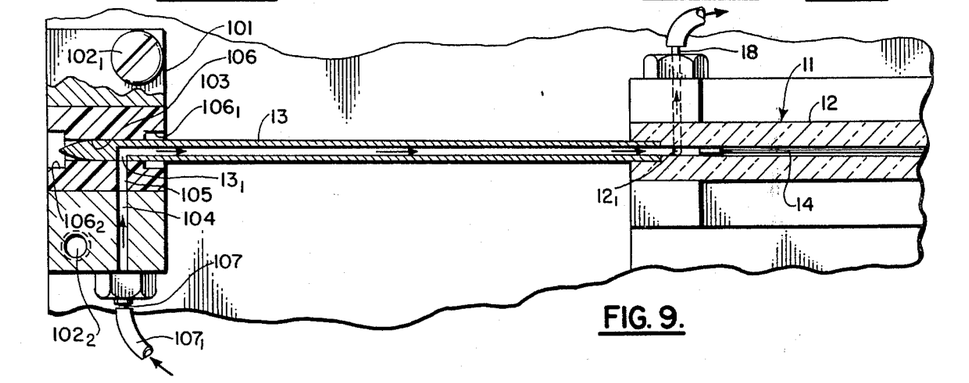
FIG. 9 details in partial section the forward end of the injector, or syringe, inclusive of the mechanism by virtue of which the fluid specimen, or sample, can be passed into the said injector for cleaning, and for loading.

The fluid specimen, as shown by reference to FIG. 9, passes via inlet 104 into side opening $13_1$ of the needle 13, passes through the hollow needle to opening $12_1$ near the rearward end of the needle 13 and exits, passing via lines 16, 18 to the exterior. Such flow is continued for a time sufficient to clean and purge the needle 13 of any possible prior contamination, after which time the valved line 18 is again closed to interrupt and cause discontinuance of such flow through line 18. At this point in time the plunger 14 of syringe 12 can be withdrawn a preselected distance to fill the barrel with a predetermined quantity of the fluid specimen.

Figure 10:
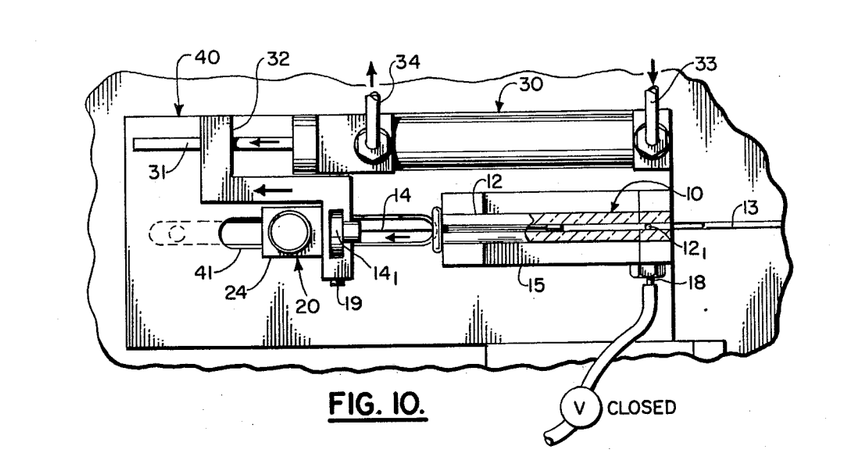
FIGS. 10, 11 and 12 depict the injector in partial section, inclusive of plunger adjustment and plunger drive mechanisms, and an injector, or syringe drive mechanism which, taken in connection with FIG. 9, illustrates in detail the operation and function of the injector, or syringe, in the injection of a fluid specimen.
Figure 13:
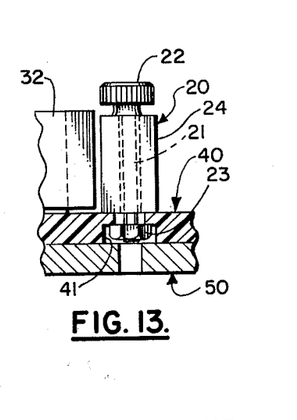
FIG. 13 is a fragmentary view in partial cross-section of the plunger adjustment mechanism, the view being a section taken along line 13—13 of FIG. 1.

(d) Referring to FIG. 10, pressurized air is now injected into line 33 of double acting cylinder piston unit 30 causing the projection of piston 31, as air is exhausted from line 34. The bracket 32 is thus moved rearward, and since it is connected to plunger handle $14_1$ of plunger 14, this causes the withdrawal of plunger 14 of syringe 12. Since the fluid specimen cannot escape through valved line 18, which is now closed, it flows into and fills that portion of the base of the barrel vacated by the retreating plunger 14. The rearward movement of the plunger 14, after it has moved a preset distance, is interrupted by impingement against block 24 of plunger adjustment means 20 (FIG. 13). The stage is now set for the insertion of the needle 13 of the syringe with the septum inlet 120, as specifically discussed with reference to FIG. 11.

Referring momentarily again to FIG. 8, as the lower face of the enlarged stem portion 91 bottoms out by contact with plate 50, the downward movement of probe 80 is discontinued. The direction of movement of probe 80 is then reversed by injection of pressurized air into inlet 78 of cylinder piston unit 71. The upward movement of stem 91 again closes the valve 89 an cuts off the flow of pressurized gas to primary inlet 86. This also discontinues the flow of gas to gas outlet 87, and line $87_1$.

Figure 11:
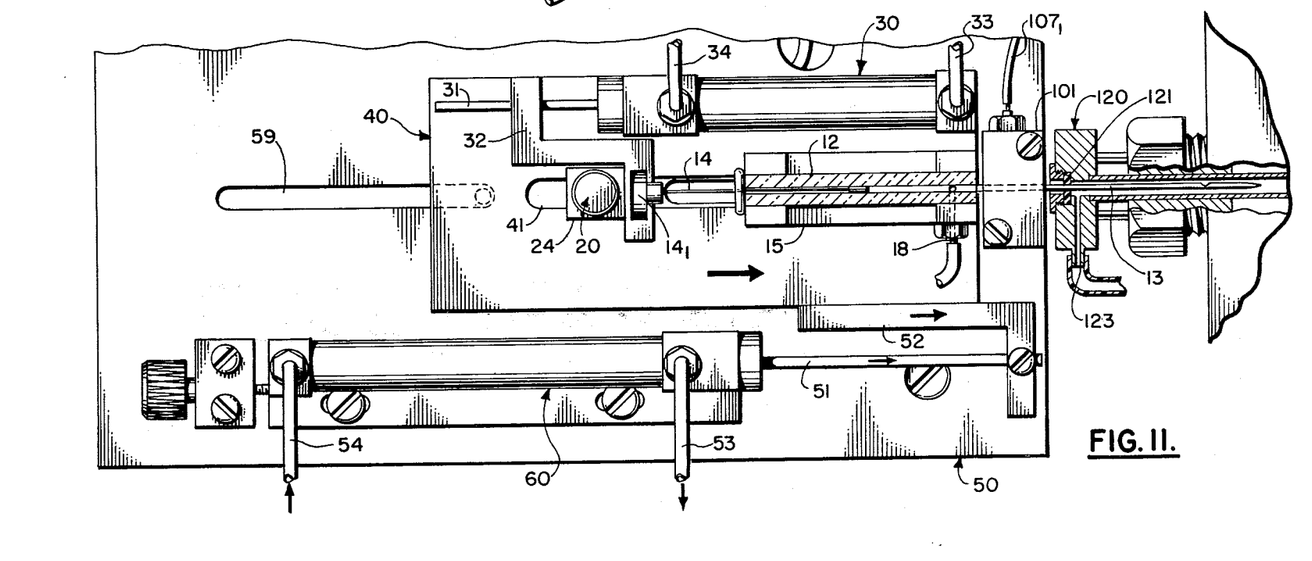

(e) Referring to FIG. 11, pressurized air is injected into line 54 of cylinder piston unit 60, air being exhausted from line 53 as piston 51 is thrust forward. The movement of piston 51, since it is appended via the connecting bracket 52 to slide plate 40, carries slide plate 40 forward along a straight line path with the several components, or sub-assemblies mounted thereon. As this occurs, the needle 13 is thrust into the septum inlet 120, piercing an inlet septum 121 which leads into an automatic instrument, e.g., a gas chromatograph.

Figure 12:
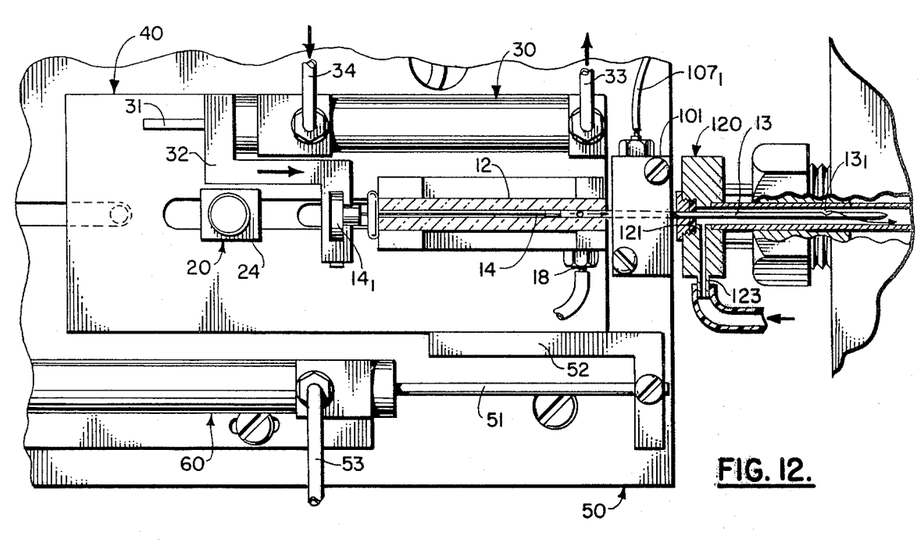

(f) Referring to FIG. 12, the preselected, accurately measured fluid specimen contained within the syringe 12 is now injected via actuation of cylinder piston unit 30. Pressurized air is now injected via line 34 into cylinder piston unit 30, air being exhausted from line 33, as piston 31 is moved forward thereby exerting a forward thrust on plunger 14, through mounting bracket 32 through which piston 31 and plunger 14 are connected. Fluid specimen is forced out of the forward opening $13_1$ of needle 13, the specimen being carried into the instrument via a carrier gas injected into the septum inlet 120 via line 123.

The needle 13, after injection of the fluid specimen, is withdrawn by injection of pressurized air via line 33 into cylinder piston unit 30, air being exhausted therefrom via line 34 as piston 31 is retracted. The withdrawal of the plunger 14 of syringe 12 stops on contact of the bracket 32 against block 24 of the plunger adjustment mechanism 20. The slide plate 40 is next repositioned by actuation of cylinder piston unit 60. Air is thus injected into line 53 of the cylinder piston unit 60, air being exhausted via line 54 as piston 51 is retracted. Retraction of piston 51 moves the slide plate 40 rearwardly until this motion is interrupted by contact of the inner face of bracket 52 with the forward end of the cylinder wall of cylinder 60.

It is apparent that various modifications and changes can be made without departing the spirit and scope of the present invention. The apparatus is constructed of materials substantially inert or nonreactive to the chemical or corrosive action of the fluid specimens to be measured and dispensed. The barrel of the syringe is normally constructed of glass, but can be constructed of a plastic or plastic-like material. The seals used in the instrument are normally constructed of plastic, and the rest of the syringe of various metals.

The seals are preferably formed of a rigid or semi-rigid, resilient form of plastic or plastic-like material. The self-lubricated plastics are especially preferred in this capacity, and can also be applied as a laminate or protective film. The polyfluorinated ethylene polymers, notable among which is polytetrafluoroethylene (Teflon), are particularly outstanding. Conventional resilient or elastic-like materials, such as natural or synthetic rubber, can also be employed.

The plunger adjustment assembly, the needle of the syringe, the cylinder-piston units, and the like, are preferably constructed of metals, e.g., ferrous metals such as iron, iron alloys, steel, stainless steels, and the like; or such metals as aluminum, magnesium, brass, copper, bronze, chrome, alloys of these and other metals, and the like.

It is apparent that various changes, such as in the absolute or relative dimensions of the parts, materials used, and the like, as well as the suggested mode of withdrawing or delivering fluids, can be made without departing the spirit and scope of the invention, as will be apparent to those skilled in this art.

Having described the invention, what is claimed is:

1. In apparatus for repetitively measuring and injecting preselected quantities of fluid specimens into a media such as an inlet to an analytical instrument, the combination comprising a base plate, constituting a portion of a housing, which can be mounted adjacent the inlet leading into the analytical instrument, a syringe sub-assembly inclusive of a tubular member mounted upon said base plate, said member being provided with an opening which contains a tubular seal, the axial opening within said tubular seal being aligned upon said inlet leading into the analytical instrument and being communicated with a lateral opening which extends through said tubular member and seal, a slide plate mounted upon said base plate, movable in the direction of said tubular member, a needle syringe mounted upon said slide plate, said syringe including a barrel within the forward end of which is mounted a hollow needle provided with a forward opening, the needle being extendable into the axial opening of the seal within said tubular member on movement of said syringe, and within the rearward end of which syringe is mounted a reciprocable plunger, a means mounted upon said slide plate for actuating and driving the plunger of said syringe, a means mounted on said base plate operatively engaged with said slide plate for reciprocal movement thereof, a magazine inclusive of means for transporting a fluid specimen contained in a vial, with a resilient, puncturable closure, an injector feed sub-assembly inclusive of a probe assembly comprised of a cylinder piston unit, the piston end of which is projected upwardly and affixed via connecting means to the probe assembly, the probe assembly being comprised of one or more downwardly directed hollow probes which are projectable for penetration of said puncturable closure of a fluid specimen containing vial delivered into position below and in the path of a hollow probe by the magazine which is located below the base plate, an upper opening within a probe being communicated with a pressurized gas source for conveyance of pressurized gas via the lower opening within said probe into the vial, an upper opening of a probe being communicated with the lateral opening within the tubular member of the syringe sub-assembly for conveyance of the fluid specimen from the vial via the lower opening within said probe to the dispensing end of the needle of the syringe, and an on-off valve which can be actuated to initiate the flow of pressurized input gas to the probe used for pressurizing the vial, whereby, on thrust of the dispensing end of the needle into said tubular member of the syringe sub-assembly via activation of the actuation and drive means which produce movement of the slide plate, and on penetration of the puncturable closure of a vial by a probe, a pressurized fluid can be injected through a probe into the vial to pressurize the fluid specimen contained therein, the fluid specimen then transferred from the vial via a hollow probe to the lateral opening within said tubular member to the opening within the dispensing end of the needle, to purge, clean and fill the syringe with a preselected quantity of the fluid specimen for subsequent injection.

2. The apparatus of claim 1 wherein the syringe sub-assembly also includes means for adjusting the distance of movement of the plunger, such that the plunger moves through a preselected distance for withdrawing and injecting fluid specimens.

3. The apparatus of claim 2 wherein said plunger adjustment means is constituted of a member which can be adjustably moved and secured in place upon the slide plate within the path of movement of the plunger to physically restrict and impede movement of the plunger after it has traversed a predetermined distance.

4. The apparatus of claim 1 wherein, within the syringe sub-assembly the means mounted upon said slide plate for actuating and driving the plunger of said syringe, and the means mounted on said base plate operatively engaged with said slide plate for reciprocal movement thereof are constituted of cylinder piston units.

5. The apparatus of claim 1 wherein the probe assembly of the injector feed assembly is comprised of a pair of parallel aligned hollow probes which are projectable through a seal contained within the base plate for penetration of the puncturable closure of a fluid specimen containing vial delivered into position by the magazine, the upper opening within one probe being communicated with a pressurized gas source for conveyance of pressurized gas via the lower opening within said probe into the vial, the upper opening of the other probe being communicated with the lateral opening within the tubular member of the syringe sub-assembly for conveyance of the fluid specimen from the vial via the lower opening within said probe to the dispensing end of the needle of the syringe.

6. The apparatus of claim 5 wherein the pair of probes are concentrically mounted one within the other.

7. The apparatus of claim 5 wherein that portion of the probe assembly which actuates the on-off valve that causes the flow of pressurized input gas to the probe used for pressurizing the vial is the connecting means comprising a cross beam which carries the probe assembly.

8. The apparatus of claim 7 wherein the valve is mounted on the base plate, is upwardly faced, biased in closed position, and is provided with a guide stem on which the end of the cross beam is slidably fitted, the lower portion of the guide stem being enlarged such that in the upward position of the cross beam the valve is closed and in the downward position of the cross beam the valve is opened by engagement of the cross beam with the enlarged portion of the stem.

9. The apparatus of claim 1 wherein the magazine is mounted below the base plate, the means for transporting the fluid specimen is constituted of a block containing one or more upwardly faced openings arrayed along a straight line path, and the block is mounted upon the piston of a cylinder piston unit, projection of which determines the straight line path.

10. The apparatus of claim 9 wherein the block contains a single upwardly faced opening, said block is mounted on the piston of a double acting cylinder piston unit, and projectable to provide a vial loading position and retractable to provide a probe pickup position.

* * * * *